United States Patent [19]

Shimp et al.

[11] Patent Number: 4,784,657

[45] Date of Patent: Nov. 15, 1988

[54] SYRINGE-VIAL MATERIAL TRANSFER INTERCONNECTOR

[75] Inventors: Lawrence A. Shimp; L. Brian Starling, both of Golden; Frank L. Cordova, Littleton, all of Colo.

[73] Assignee: Ceramed Corporation, Lakewood, Colo.

[21] Appl. No.: 939,576

[22] Filed: Dec. 9, 1986

Related U.S. Application Data

[63] Continuation of Ser. No. 782,407, Oct. 1, 1985, abandoned.

[51] Int. Cl.[4] .............................................. A61B 19/00

[52] U.S. Cl. .................................. 604/407; 604/403; 604/57; 604/58

[58] Field of Search .................... 604/403, 407, 59-60, 604/57, 58, 61, 62, 77-79

[56] References Cited

U.S. PATENT DOCUMENTS

| | | | |
|---|---|---|---|
| 342,837 | 6/1886 | Olson | 604/407 |
| 2,826,198 | 3/1958 | Van Sickle | 604/59 |
| 3,873,274 | 3/1975 | Neisius | 604/407 |
| 3,980,074 | 9/1976 | Watt et al. | 604/58 |
| 4,046,145 | 9/1977 | Choksi et al. | 604/407 |
| 4,230,112 | 10/1980 | Smith | 604/403 |
| 4,237,884 | 12/1980 | Erickson et al. | 604/77 |
| 4,317,448 | 3/1982 | Smith | 604/403 |
| 4,551,135 | 11/1985 | Gorman et al. | 604/57 |

*Primary Examiner*—C. Fred Rosenbaum
*Assistant Examiner*—H. Macey
*Attorney, Agent, or Firm*—Glenn K. Beaton

[57] ABSTRACT

An interconnect connects a vial to a syringe for the transfer of material to the syringe or back to the vial. The interconnect includes a vial connecting mechanism and a tapered sleeve to receive the syringe. A metering port allows control of the material transfer rate and prevents partial transfers which could cause material spillage.

8 Claims, 1 Drawing Sheet

SYRINGE-VIAL MATERIAL TRANSFER INTERCONNECTOR

This is a continuation of co-pending application Ser. No. 782,407 filed on Oct. 1, 1985 and now abandoned.

This invention relates to devices for transferring granules or other loose solids from a vial to a syringe.

BACKGROUND AND SUMMARY OF THE INVENTION

Syringes are commonly filled with liquids by immersing a needle on the end of the syringe below the liquid level in a vial and then withdrawing the syringe plunger. The differential air pressure between the liquid surface and the syringe cylinder interior forces liquid up through the needle and into the syringe. The vial may include a flexible membrane over the top which is penetrated by the syringe needle and which seals upon withdrawal of the needle.

Granules such as hydroxylapatite granules and other loose solids cannot be transferred to a syringe in the manner described above for liquids because the body of granulated material will not support a differential air pressure. Instead, granules are typically transferred by pouring them from the vial into the inverted syringe. Funnels have been used to help prevent spilling the granules while they are poured. In some cases, the funnels have been attached to the vial or have been manufactured to fit closely over the syringe opening, but no existing methods integrally connect the syringe to the vial.

The existing granule transfer methods are inadequate in several respects. All the existing methods normally require two hands, while the person filling the syringe may have only one hand free. The existing methods do not include a simple method for re-transferring granules from the syringe to the vial in case too much is initially transferred to the syringe. The existing methods do not effectively prevent granules from being spilled during transfer because there is no seal between the vial and the syringe.

The method described above is also inadequate for transferring liquid to syringes without a needle. When a syringe without a needle is removed from the liquid, the large syringe opening allows the withdrawn liquid to flow out of the syringe.

This invention overcomes these inadequacies of the existing methods. Vials or bottles (both of which are referred to as "vials" herein) are fitted with an interconnect device featuring a tapered sleeve to receive the end of a syringe. The seal between the tapered sleeve and the syringe prevents any spilling. The material may be transferred with one hand by inverting the assembly. The granules may be re-transferred to the vial by simply turning the assembly right-side-up, again without spilling. A metering port in the device between the tapered sleeve and the vial interior allows close control of the transfer rate and prevents material from coming to rest in the sleeve where it could be spilled upon disengaging the syringe from the sleeve. The interconnect device is capped after removal of the syringe by a friction fit shaft or a deformable plug.

To one skilled in this art who has the benefits of the invention's teachings, other features and advantages of this invention will be apparent from the following description of the presently preferred embodiments of the invention, given for the purpose of disclosure in conjunction with the accompanying drawings.

DESCRIPTION OF PREFERRED EMBODIMENTS

Figure 1:
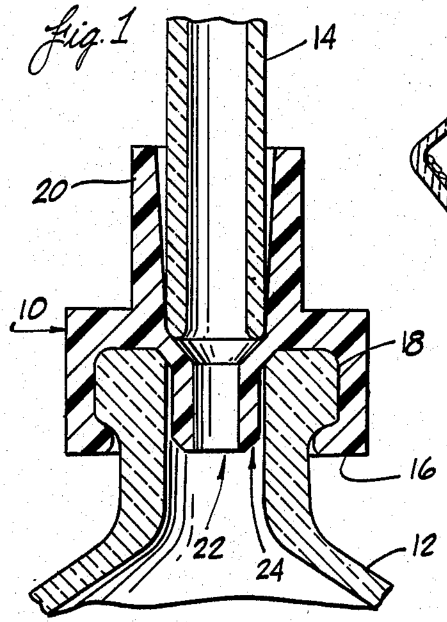
FIG. 1 shows a sectional view along the center axis of the interconnect device, attached to a vial with a syringe and engaged in the interconnect sleeve.

Referring to FIG. 1, the interconnect 10 is shown in conjunction with the top of a vial 12 and the end of a syringe 14. In this preferred embodiment, the interconnect 10 is molded from flexible medical grade plastic. Other usable materials will be apparent to those skilled in the art. The interconnect has an annular bottom ridge 16 that snap fits over the top flange 18 of the vial 12. Alternatively, the interconnect may have a threaded bottom to mate with the top of a threaded vial.

A sleeve 20 at the interconnect top has an interior taper toward the vial to receive and form a granule seal with the syringe 14. The taper in the sleeve allows the sleeve to receive and form a granule seal with syringe ends of different diameters. Thus, the invention will accommodate syringes of different sizes or syringes of the same size with different diameters caused by manufacturing variances. This preferred embodiment uses a sleeve taper of approximately two degrees from the longitudinal axis of the sleeve. Other tapers are also effective depending on the length of the sleeve, the range of syringe diameters the sleeve is to accommodate, and the desired seal between the sleeve and the syringe. For example, tapers of twelve degrees will result in a sleeve that will accommodate a large range of syringes, but the sleeve-syringe seal will be compromised. At the other extreme, a zero degree taper will result in an excellent seal, but only for a single syringe diameter.

At the bottom of the interconnect 10 is a metering port 22 fitting into the neck of the vial 12 to partially obstruct the flow of material out of the vial and into the syringe. The bottom end 24 of the metering port 22 may be flat or may be bevelled toward the inner or outer surface. A bevel on the inner surface will lessen the flow obstruction and a bevel on the outer surface will increase the flow obstruction.

The granules are transferred from the vial 12 to the syringe 14 by snapping the interconnect 10 onto the vial top 12, inserting the syringe end 14 into the interconnect sleeve 20, and partially inverting the assembly. When the desired amount of material has been transferred, the tilt angle of the assembly is reduced until the transfer terminates and the syringe end 14 is disengaged from the interconnect sleeve 20.

Figure 3:
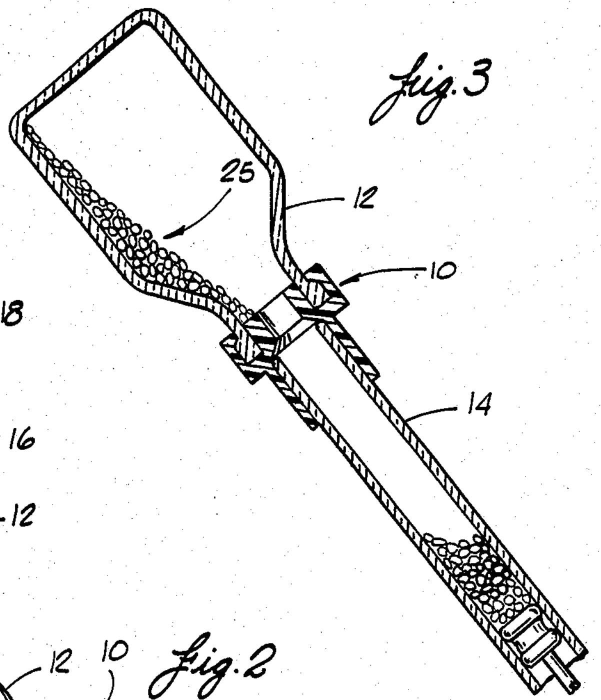
FIG. 3 shows a side plan view of the vial-interconnect-syringe assembly with a metering port, being inserted to transfer material (in this case granules) to the syringe.
Figure 2:
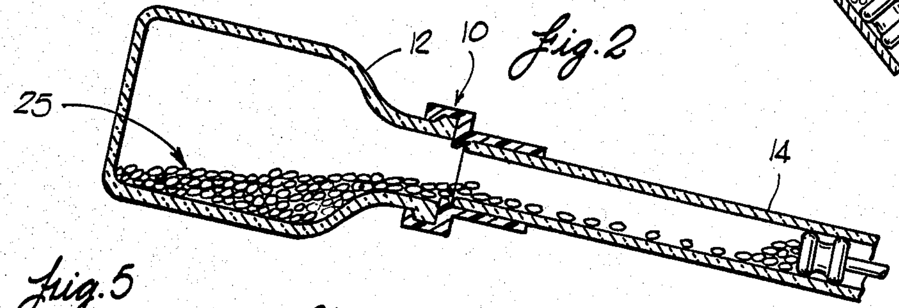
FIG. 2 shows a side plan view of the via-interconnect-syringe assembly without a metering port, being inverted to transfer material (in this case granules) to the syringe.

FIGS. 2 and 3 further illustrate the operation of the interconnect 10 for transferring solid granules and, especially, the metering port 22. FIG. 2 shows the vial-interconnect-syringe assembly without a metering port. As the assembly is inverted to a tilt angle above horizontal, the granules 25 immediately sift along the interconnector and the length of the syringe. The assembly is moved to a horizontal position after the desired amount of granules 25 have been transferred. When the syringe 14 is disengaged from the interconnect sleeve 20 in the horizontal position, some of the granules left in the interconnector 10 and along the length of the syringe near the end of the syringe 14 are likely to spill out.

As illustrated in FIG. 3, the metering port avoids spilling upon syringe disengagement. The metering port 22 prevents the granules from dropping into the syringe until a predetermined tilt angle is attained. The angle depends on the bevel of the metering port bottom 24 and the inside diameter of the metering port 22. The desired tilt angle is the angle which will force the dropping granules 25 to drop to the bottom of the syringe 14 without collecting along the length of the syringe 14. Thus, after the desired amount of granules 25 have been transferred and the tilt angle of the assembly is reduced to terminate transfer, the syringe 14 may be disengaged from the interconnect sleeve 20 with no danger of granules being spilled. It has been found that for dry granules of hydroxylapatite a tilt angle of approximately 60 degrees from horizontal is sufficient to prevent any granules from collecting along the length of the syringe. This angle is achieved with no bevel on either side of the metering port bottom 24. Other types of granules may require other tilt angles to avoid granules collecting along the length of the syringe, and thus other bevels on the metering port bottom 24 or diameters in the metering port 22. While the drawings illustrate the operation of the apparatus for transferring solid granules, a similar operation with similar advantages is used for liquid transfer.

Figure 4:
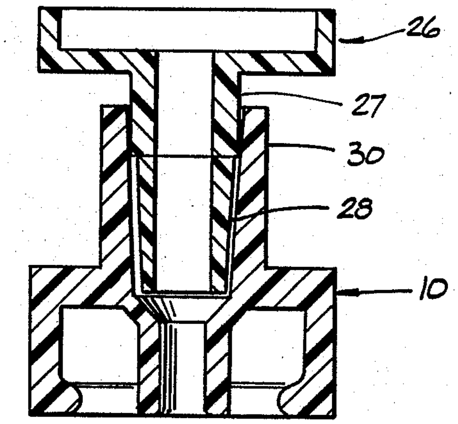
FIG. 4 shows a sectional view along the center axis of the interconnect device and cap.

FIG. 4 shows the interconnect cap 26 inserted into the interconnect sleeve 20. The cap has a stopper 27 with a tapered portion 28 tapering toward the vial at an angle in excess of the taper of the interconnect sleeve 20. In the preferred embodiment, a taper of approximately three degrees from the stopper longitudinal axis is used. The stopper 27 also includes a shaft 30 at the upper end. The diameter of the shaft 30 matches the diameter of the opening at the top of the sleeve 20. The cap 26 is positioned by removing the syringe end 14 from the interconnect sleeve 20, and inserting the stopper tapered portion 28. The stopper shaft 30 is then pressed into the interconnect sleeve 20 by applying a downward force to the top of the cap 26 until the desired friction fit is attained. The seal between the interconnect 10 and the cap 26 is improved if the stopper 27 is sized so that the bottom edge of the stopper shaft 30 contacts the bottom of the sleeve 20 when the stopper shaft 30 is inserted into the sleeve 20. The stopper tapered portion 28 permits the cap 26 to be temporarily rested on the interconnect 10 without the step of pressing the stopper shaft 30 into the interconnect sleeve 20. The taper on the stopper tapered portion 28 helps ensure that its surface does not contact the interconnect sleeve 20. Such contact could distort the interconnect sleeve 20 and thereby prevent the syringe end 14 from fitting properly.

Figure 5:
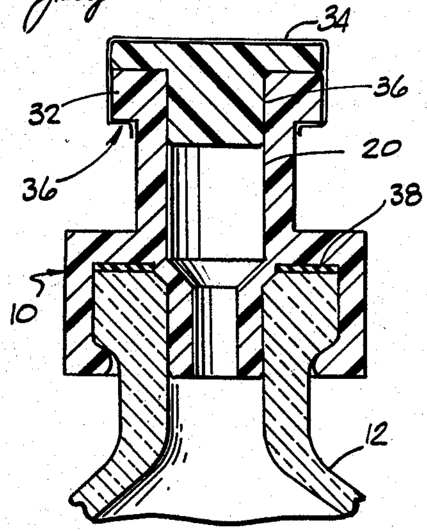
FIG. 5 shows a sectional view along the center axis of an alternate embodiment of the interconnect device and cap.

In the alternative embodiment for the cap 26 and interconnect 10 shown in FIG. 5, the top of the interconnect 10 has a flange 32 in the same shape and dimensions as the top flange 18 of the vial 12. A standard rubber stopper 34 used for capping the vial 12 without the interconnect 10 may then be used to cap the interconnect 10. The straight shaft 36 of the stopper 34 deforms to the shape of the interconnect tapered shaft 20 to provide an airtight seal between the stopper and the interconnect. The stopper 34 may include a crimped metal seal 36 that is crimped around the interconnect flange 32. In a variation of this alternative embodiment, not shown in the drawings, the interconnect may have a threaded top on the sleeve to mate and seal with a threaded annular surface on the cap. In any of these embodiments, a flexible ring gasket 38 may be compressed between the top of the vial flange 18 and the interconnect 10 to form an airtight seal between the interconnect 10 and the vial 12.

While the invention has been disclosed in connection with the preferred embodiments thereof, it should be understood that certain changes may be made which are within the spirit and scope of the invention as defined by the following claims:

What is claimed is:

1. A method for the regulated gravity transfer of solid granule material between a vial and a syringe, comprising the steps of attaching the syringe to the vial with an interconnector having a generally tubular conduit with an annular surface on the upper opening to receive the syringe and a lower opening in communication with the vial interior, said tubular conduit having an annular flow-impeding port in said lower opening with a constant cross-section aperture and a granular flow-impeding annular shoulder on its lower side to impede the flow of granules from the vial to the syringe; partially inverting the assembled syringe, interconnector and vial so that said vial is at a higher level than said syringe, and striking said assembly to disturb the equilibrium of the granules, to allow the gravity transfer of granules from the vial past the flow-impeding port and through said tubular conduit and into the syringe; returning the assembled syringe, interconnector and vial to a partially upright position to prevent the gravity transfer of granules past the flow-impeding port; and detaching the syringe from the interconnector.

2. The method of claim 1 wherein the dimensions of said flow-impeding port aperture, and the angle between the longitudinal axis of said tubular conduit and the surface of said flow-impeding port shoulder, are predetermined whereby the lowest inversion angle required for granules to flow through said flow-impeding port is higher than the highest inversion angle at which significant amounts of granules will rest in the tubular conduit or adjacent the syringe opening.

3. The method of claim 2 wherein said predetermined angle between the longitudinal axis of the tubular conduit and the surface of the flow-regulating port shoulder is a bevel on the exterior circumference of said port.

4. The method of claim 2 wherein said predetermined angle between the longitudinal axis of the tubular conduit and the surface of the flow-regulating port shoulder is substantially perpendicular to the longitudinal axis of said tubular conduit.

5. The method of claim 2, wherein said interconnector has a vial connecting annular ridge contoured to mate with a vial flange on said vial, and wherein said annular surface to receive the syringe is a syringe sealing sleeve tapering from a bottom interior diameter less than the exterior diameter of said syringe to a top interior diameter greater than the exterior diameter of said syringe at an angle between 0° and 12° from the longitudinal axis of said tubular conduit.

6. The method of claim 5, wherein said interconnector includes a stopper with a shaft, the shaft distortably inserted into said sleeve and having an upper diameter approximately equal to the top interior sleeve diameter and a tapered portion below the upper portion, the tapered portion having a taper greater than the taper of said sleeve and the bottom of the tapered portion being in contact with the interior of the sleeve when the shaft is inserted into the sleeve.

7. The method of claim 6, wherein said interconnector includes an interconnector flange around the outer top of the interconnector, a metal crimper around the outer top of the stopper for crimping onto the interconnector flange and a flexible gasket ring compressed between the vial flange and the interconnector.

8. The method of claim 5, wherein the interior of said sleeve tapers to match the exterior of a tapered sleeve on the syringe, and wherein said interconnector includes a stopper with a shaft, the shaft distortably inserted into the sleeve and having a diameter approximately equal to the top interior sleeve diameter, an interconnector flange around the outer top of the interconnector, and a metal crimper around the outer top of the stopper for crimping onto the interconnector flange.

* * * * *